United States Patent [19]

Imamura et al.

[11] Patent Number: 6,017,746

[45] Date of Patent: Jan. 25, 2000

[54] **REMEDYING A CONTAMINATED ENVIRONMENT USING *PSEUDOMONAS CEPACIA* OR *CORYNEBACTERIUM SPECIES* AND *RENOBACTER* SPECIES FERM BP-5353 HAVING DEHALOGENASE ACTIVITY**

[75] Inventors: Takeshi Imamura, Chigasaki; Tetsuya Yano, Isehara, both of Japan

[73] Assignee: Canon Kabushiki Kaisha, Tokyo, Japan

[21] Appl. No.: 08/868,951

[22] Filed: Jun. 4, 1997

Related U.S. Application Data

[62] Division of application No. 08/561,237, Nov. 21, 1995, Pat. No. 5,679,568.

[30] Foreign Application Priority Data

| Nov. 21, 1994 | [JP] | Japan | 6-286234 |
| Nov. 21, 1994 | [JP] | Japan | 6-286235 |
| Nov. 22, 1994 | [JP] | Japan | 6-288300 |

[51] Int. Cl.[7] .................. B09B 3/00; C12N 1/00; C12N 1/12; C12N 1/20
[52] U.S. Cl. ........... 435/252.1; 210/601; 435/252.34; 435/252.4; 435/253.3; 435/262.5; 435/822; 435/843; 435/874
[58] Field of Search .................. 435/262.5, 183, 435/248, 252.1, 252.34, 252.4, 253.6, 261, 264, 821, 843, 874, 822; 210/601

[56] References Cited

U.S. PATENT DOCUMENTS

| 4,535,061 | 8/1985 | Chakrabarty et al. | 435/253 |
| 4,804,629 | 2/1989 | Roy | 435/253.3 |
| 4,816,403 | 3/1989 | Roy | 435/253.3 |
| 4,959,315 | 9/1990 | Nelson et al. | 435/167 |
| 5,470,742 | 11/1995 | Bull et al. | 435/262 |
| 5,578,474 | 11/1996 | Focht et al. | 435/172.3 |

FOREIGN PATENT DOCUMENTS

| 0179603 | 4/1986 | European Pat. Off. . |
| 0481963 | 4/1992 | European Pat. Off. .......... C02F 3/34 |
| 0694527 | 1/1996 | European Pat. Off. ...... C07C 227/40 |
| 4-64544 | 2/1992 | Japan . |
| 2045748 | 11/1980 | United Kingdom ............ C07C 27/00 |

OTHER PUBLICATIONS

Negoro et al., "Growth of Microalgae . . . and No$_x$", Appl. Biochem. and Biotech., vols. 28/29, Spring 1191, pp. 877–887.
Hanson et al. Dev. of Methanothrops . . . Olefins, A.C.S.,Div. Envr. Chem, Preprint Extended Abstr., Sep. 189, pp. 365–367.
Jones et al., "Nucleotide Sequence . . . Protein," J. Gen. Microbiology, 138, 675–683 (1992).
Schneider et al., Site–Directed Mutagenesis . . . Activity, Biol. Chem, Hoppe–Seyler, vol. 374, pp. 489–495 (1993).
Journal Japan Sewage Works Assn., vol. 24, No. 273, pp. 27–33 (1987).

Motosugi et al., "Enzymological Aspects of Halo Acid Dehalogenation", Protein, Nucleic Acid and Enzyme, vol. 29, No. 2, 1984 (ISSN 0039–9450 pp. 101–110.
Nakajima et al., "Novel Metabolite . . . Pathway", Biosci., Biotech. Biochem., 56 (3), 486–489, 1992.
Nakajima et al., Purification and Properties . . . Methylocystis, Biosci. Biotech. Biochem., 56 (5), 736–740, (1992).
Uchiyama et al., "Aerobic Degradation . . . Strain M", Agr. Biol. Chem. 53 (11), 2903–2907, 1989.
Winter et al., "Efficient Degradation . . . *E. coli*", Bio. Technology, vol. 7, Mar. 1989, pp. 282–285.
Vannelli et al., "Degradation of Halogenated Aliphatic. . . europea", Appl. & Envir. Micro., vol. 56, No. 4, Apr. 1990, pp. 1169–1171.
Wackett et al., "Degradation of Trichloroethylene . . . Pseudomonas putida F1", Appl. & Envir. Micro., vol. 54, No. 7, Jul. 1988, pp. 1703–1708.
Vandenbergh et al., "Metabolism of Volatile . . . Pseudomonas fluorescens", Appl. & Envir. Micro,m vol. 54, No. 10, Oct. 1985, pp. 2578–2579.
Gannon et al., "Relationship between . . . through soil", Appl. & Envir. Micro., vol. 57, No. 1, Jan. 1991, pp. 190–193.
Kamath et al., "New Pathway . . . niger", Appl. & Envir. Micro., vol. 56, No. 1, Jan. 1990, pp. 275–280.
Little et al., Trichloroethylene Biodegradation . . . Bacterium, Appl. & Envir. Micro., vol. 54, No. 4, Apr. 1988, pp. 951–956.
Nelson et al., "Aerobic Metabolism . . . Isolate", Appl. & Envir. Micron., vol. 52, No. 2, aug. 1986, pp. 383–384.
Nelson et al., "Biodegradation of Trichloroethylene . . . Pathway", Appl. & Envir. Micro., vol. 53, No. 5, May 1987, pp. 949–954.
Hsien–Chyang Tsien, et al., Biodegradation of Trichloroethylene . . . OB3b, Appl. & Envir. Micro., vol. 55, No. 12, Dec. 1989, pp. 3155–3161.

(List continued on next page.)

*Primary Examiner*—David M. Naff
*Assistant Examiner*—Deborah K. Ware
*Attorney, Agent, or Firm*—Fitzpatrick, Cella, Harper & Scinto

[57] ABSTRACT

A process for remedying an environment contaminated with an aliphatic organochlorine compound which includes the use of *Pseudomonas cepacia* strain KK01 (FERM BP-4235) or Corynebacterium species (FERM BP 5102) and Renobacter species (FERM BP-5353). The first two microorganisms are capable of introducing an oxygen atom into the aliphatic organochlorine compound in order to convert the aliphatic compound to an epoxide. During protonization the epoxide is converted into a chlorinated organic acid. Renobacter species strain FERM BP-5353 decomposes chlorinated organic acids to substances naturally existing in nature. The chlorinated and/or halogenated acids include chloroacetic acid, dichloroacetic acid, trichloroacetic acid and dichloropropionic acid, etc. The polluted environments in which the processes may be carried out include the soil, ground water and waste water.

3 Claims, 8 Drawing Sheets

OTHER PUBLICATIONS

Doronina et al., "Composition of the Biomass . . ." AN:87:125160 Biosis 22(4) 1986, 557–561.

Heinze et al., "Biodegradation of Dichloroacetic Acid . . . ", Appl. Microbiol. Biotech., 40:158–164 (1993).

Meusel et al., "Biodegradation of Dichloroacetic Acid . . . ", Appl. Microbiol. Biotech. 40:165–171 (1993).

Nakajima et al., "Novel Metabolite of Trichloroethylene . . . Pathway", Biosci. Biotech. Biochem., 56 (3), 486–489, 1992.

Meusel et al., "biodegradation of Dichloroacetic acid . . . in Soil", Appl. Microbiol. Biotechnol. (1993) 40:165–171.

6,017,746

REMEDYING A CONTAMINATED ENVIRONMENT USING *PSEUDOMONAS CEPACIA* OR *CORYNEBACTERIUM SPECIES* AND *RENOBACTER* SPECIES FERM BP-5353 HAVING DEHALOGENASE ACTIVITY

This application is a division of application Ser. No. 08/561,237 now issued as U.S. Pat. No. 5,679,568 filed Nov. 21, 1995, now U.S. Pat. No. 5,679,568.

BACKGROUND OF THE INVENTION

1. Field of the Invention

This invention relates to a process for decomposing a pollutant using a microorganism, particularly a process for decomposing a halogenated organic compound using a microorganism which has an activity to decompose the halogenated organic compound, to a process for environment remediation, which can decompose a pollutant in the environment, such as ground water, soil and so on, and to a microorganism capable of decomposing a pollutant and being used in the decomposition and remediation processes.

2. Related Background Art

The by-products resulting from the disinfection process of city water have been a serious concern since the U.S. Environmental Protection Agency reported on them in the 1970s. In Japan also, where chlorination of city water is compulsory, the by-products such as trihalomethanes, halogenated acetic acids, halogenated acetonitriles and halogenated ketones have been detected in city water, and has become a great problem because of their liver toxicity and mutagenicity. Particularly halogenated organic acids, for example halogenated acetic acids such as chloroacetic acid, dichloroacetic acid, trichloroacetic acid and bromoacetic acid have been designated as environment surveillance items in Japan since 1993, attracting a great deal of attention as a new problem. Details are reported in "Analytical Methods for Revised Standards of Water Quality and Environment" in the Proceedings of the 23rd Seminar of Water Environment Society of Japan (Incorporated Association of Water Environment Society of Japan), November 1993, pp.55–64.

These halogenated organic acids cannot be degraded by aeration. As one of the countermeasures, for example, biodegradation treatment such as a bioreactor is very useful because treatment can be conducted under mild conditions and is relatively low in cost.

Microorganisms having a decomposing activity of halogenated organic acids have been studied, for example, molds such as Trichoderma, Acrostalagmus, Penicillium and Clonostachys, and bacteria such as Pseudomonas, Arthrobacter, Rhizobium, Agrobacterium, Bacillus, Alcaligenes, Nocardia, Micrococcus, Achromobacter and Moraxella (Protein, Nucleic Acid and Enzyme (1984), vol.29, p.101–110). Adachi reported that an unidentified strain OS-2 has an enzyme which can decompose chloroacetic acid, bromoacetic acid and iodoacetic acid to about the same extent, and OS-2 can also decompose dichloroacetic acid though to half the extent of the above compounds (Proceedings of Osaka Prefectural Institute of Public Health, "Public Health" No. 30, p.89 (1992)). Furthermore, decomposition of halogenated organic acids having two to six carbons was studied using dehalogenase extracted from *Pseudomonas putida* NCIMB 12018 and immobilized on carboxymethyl cellulose or thioglycolic acid. (European Patent No. 179603).

The relation between dehalogenating enzymes for decomposing halogenated organic acids and their genes has been studied using *Pseudomonas putida* AJ1 strain (J.Gen. Microbiol., 138, p.675 (1992)), *Pseudomonas cepacia* MBA4 strain (J.Biochem., 284, p.87 (1992)) and Pseudomonas sp. CBS3 strain (Biol. Chem. Hoppe-Seyler., 374, p.489 (1993)).

All these studies are done on the enzyme level, and not on the actual behavior of the microorganisms in the polluted waste water. Concerning the microbial decomposition of halogenated organic acids, only *Xanthobacter autotrophicus* GJ10 strain (Appl. Biochem. Biotechnol., 40, 158 and 40, 165 (1993)) has been studied.

Japanese Patent Laid-Open Application No. 4-64544, discloses dehalogenase extracted from Pseudomonas which decomposes D- and L-chloropropionic acid into lactic acid. This is, however, also a study at the enzyme level.

SUMMARY OF THE INVENTION

The present invention has been made to solve the above mentioned problems and provides a biodegradation process of halogenated organic acids and a process for remedying environment using the process.

Another object of the present invention is to provide a biodegradation process giving substantially complete decomposition of aliphatic organochlorine compounds and a process for remedying environment using the process.

Another object of the present invention is to provide a new microbial strain which is suitably used in the biodegradation process of halogenated organic acids and aliphatic organochlorine compounds and in the environment remediation using the process.

DETAILED DESCRIPTION OF THE INVENTION

Figure 1:
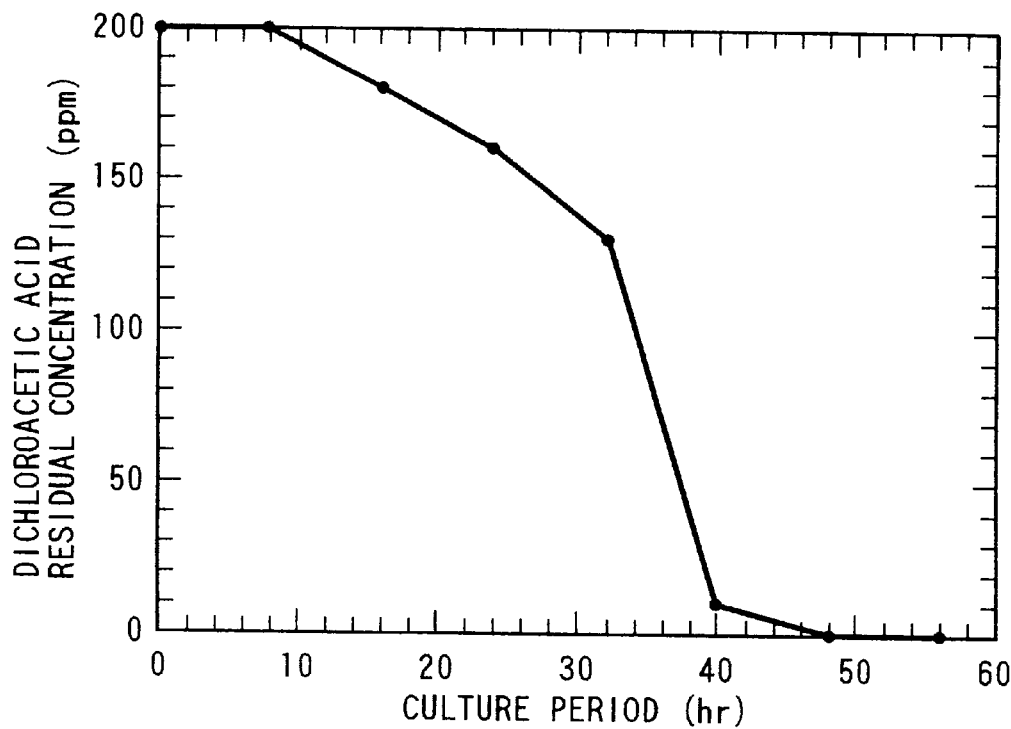
FIG. 1 is a graph showing the decomposition of dichloroacetic acid by strain AC.

The above-mentioned objects will be accomplished by the present invention described below.

Searching for microbial strains having halogenated organic acid-decomposing activity, the present inventors obtained a new microbial strain which can decompose a high concentration of halogenated organic acids, from the soil of Kanto loam layer in Japan. The present inventors have found a process for decomposing halogenated organic acids in aqueous medium by exposing it to the above strain.

The complete taxonomic description of FERM P-14641, now identified as FERM BP-5353, is as follows:

A. Morphology
   Gram stain: negative
   cell size and shape: C and/or S shape rod
      1.0–2.0 $\mu$m in length
      0.2–0.5 $\mu$m in width
   motility: none
   color of colony: white to cream
B. Growth in culture media
   BHIA: good
   MacConkey: poor
C. Optimum growth temperature: 25–35° C.
D. Physiological characteristics
   Aerobic or anaerobic: aerobic
   TSI (slant/butt): alkali/alkali, $H_2S$ (−)
   Oxidase: positive
   Catalase: positive In view of the characteristics mentioned above, the present strain is suitably classified into Renobacter sp.

As is evident from the following Examples, the present strain has an excellent activity to decompose halogenated organic acids. Since strains capable of decomposing halogenated organic acids had not been known in Renobacter species, the present strain was acknowledged as a new strain, and named Renobacter sp. AC. It was deposited in National Institute of Bioscience and Human-Technology, Agency of Industrial Science and Technology (Deposition No.: FERM BP-5353).

Strain AC is very unique in its growth style in addition to the cell shape (S-shaped). It grows forming cell aggregates secreting a certain kind of polymeric material(s) not identified yet. From the microscopic viewpoint, this characteristic allows strain AC to rapidly form its own habitat and to become a prior species in drainage, liquid wastes, rivers and lakes where various kinds of microorganisms exist and be advantageously used for decomposing halogenated organic acids in such places.

Although the present strain can be cultured in a natural complete medium such as 2YT and LB, it can also be cultured in an inorganic salt medium, for example M9, supplemented with a small amount of yeast extract as a nutrient.

The composition of M9 is as follows:
$Na_2HPO_4$: 6.2 g
$KH_2PO_4$: 3.0 g
NaCl: 0.5 g
$NH_4Cl$: 1.0 g
in 1 litter of medium (pH 7.0).

Culture can be carried out under aerobic conditions and in either liquid or solid medium. The temperature for culture is preferably about 30° C.

It is evident that any mutant spontaneously or artificially derived from the present strain is included in the scope of the present invention so long as it has a good decomposing activity for halogenated organic acids. Accordingly, examples using such a mutant are also included in the scope of the present invention.

In one embodiment of the present invention, decomposition of halogenated organic acids can be carried out by bringing in contact the above Renobacter sp. AC with halogenated organic acids in an aqueous medium such as liquid wastes and the like. It can be carried out by culturing the microorganism in the aqueous medium containing halogenated organic acids, or by adding the aqueous medium to the culture of the microorganism, using various methods such as a batch method, a semi-continuous method and a continuous method. The microorganism may be in a state semi-immobilized or full-immobilized to a suitable carrier. As described above, the present strain can be easily and advantageously immobilized because it grows into a mass secreting a polymeric material(s) by itself.

In another embodiment of the present invention, decomposition of halogenated organic acids can be carried out by bringing in contact Renobacter sp. AC with halogenated organic acids in soil. It can be conducted by culturing the strain in the soil containing halogenated organic acids or by mixing the polluted soil into the culture of the strain.

This process can be used for remedying soil both in the closed system and the open system, and the process is carried out by various methods such as batch method, semi-continuous method and continuous method. The microorganism may be in a state semi-immobilized or full-immobilized to a suitable carrier. As described above, the present strain can be easily and advantageously immobilized because it grows into a mass secreting a polymeric material(s) by itself.

The present inventors also found a process for decomposing aliphatic organochlorine compounds, for example, trichloroethylene (hereafter referred to as TCE) into substances naturally existing in nature and a process for remedying environment using the above process, applying the above-mentioned process for decomposing halogenated organic acids.

Recently, environmental pollution with aliphatic organochlorine compounds which are harmful to living bodies and hardly decomposable has become a serious problem. Particularly, it is considered that the soil in a manufacturing area of high technology industry is polluted with organochlorine compounds such as tetrachloroethylene (PCE), trichloroethylene (TCE) and dichloroethylene (DCE), and the pollution is expanding in a wide range. Actually, such organochlorine compounds were detected by environmental research and reported frequently. It is said that these aliphatic organochlorine compounds in soil are dissolved in the rain water to flow into the groundwater, thus the pollution expands to the surrounding area. These compounds are suspected of carcinogenicity, and very stable in environment. Accordingly it has been a serious social problem that ground water, which is utilized as a source of drinking water, is polluted with such compounds.

In regard to these aliphatic organochlorine compounds, especially TCE, recently a process for aerobic microbial decomposition has been reported, more particularly, a biodegradation process in which TCE is epoxidized by an oxygenase-type enzyme (Methylocystis sp. strain M containing methane monooxygenase (Agric. Biol. Chem., 53, p.2903 (1989), Biosci. Biotech. Biochem., 56, p.486 and 56, p.736 (1992)); *Methylosinus trichosporium* OB3b (Am. Chem. Soc. Natl. Meet. Dev. Environ. Microbiol., 29, p.365 (1989), Appl. Environ. Microbiol., 55, p.3155 (1989), Appl. Biochem. Biotechnol., 28, p.877 (1991)); *Pseudomonas putida* BH containing phenol hydroxylase (Journal of Sewerage Association, 24, p.27 (1987)); Acinetobactor sp. strain G4 containing toluene monooxygenase (Appl. Environ.

Microbiol., 52, p.383 (1986), 53, p.949 (1987), 54, p.951 (1989), 56, p.279 (1990) and 57, p.193 (1991)); *Pseudomonas mendocina* KR-1 (Bio/Technol., 7, p.282 (1989)); *Pseudomonas putida* F1 containing toluene dioxygenase (Appl. Environ. Microbiol., 54, p.1703 (1988) and 54, p.2578 (1988)); *Nitrosomonas europaea* containing ammonia monooxygenase (Appl. Environ. Microbiol., 56, p.1169 (1990)).

It is considered that epoxidized TCE by an oxygenase-type enzyme as listed above is further decomposed biologically or non-biologically, and glyoxylic acid and dichloroacetic acid are produced by the protonization of TCE epoxide at this stage.

Namely, TCE decomposition by a microorganism containing an oxygenase-type enzyme necessarily produces dichloroacetic acid at a certain ratio. Accordingly, by treating the resulting dichloroacetic acid with a microorganism capable of decomposing halogenated organic acids, TCE can be finally decomposed into substances originally present in the natural world.

The detailed process of the present invention is: TCE-polluted ground water or soil is simultaneously or successively treated with two kinds of microorganisms, one of which aerobically converts TCE into TCE epoxide and another one decomposes dichloroacetic acid generated at a certain ratio by the above reaction, into carbon dioxide, water and chloride ion, thus decomposing the soil and water polluting TCE into harmless substances.

The microorganism used for decomposing TCE in the present invention can be any microorganism so long as it decomposes TCE through epoxidation of TCE; therefore all of the above-mentioned TCE-decomposing strains can be used. In addition, those unidentified microorganisms, unisolated microorganisms, a group of symbiotic microorganisms and newly isolated and identified microorganisms can be also used so long as they have such a characteristic or activity as mentioned above. Already identified microorganisms having such a characteristic or activity and applicable to the present invention include bacteria of genus Pseudomonas, Acinetobactor, Xanthobacter and Corynebacterium, particularly advantageously used are *Pseudomonas cepacia, Pseudomonas putida, Pseudomonas fluorescence* and *Pseudomonas aeruginosa*. For example, *Pseudomonas cepacia* KK01 (FERM BP-4235; hereafter referred to as strain KK01) which is isolated from the intestine of *Nasutitermes takasagoensis* or Corynebacterium sp. strain J1 (FERM P-14332; hereafter referred to as strain J1).

For the microorganism for decomposing halogenated organic acids, any microorganism can be used so long as they decompose halogenated organic acids, for example, halogenated acetic acids, particularly dichloroacetic acid into substances originally present in the natural world, such as carbon dioxide, water and chloride ion; therefore the above-mentioned bacteria which decompose dichloroacetic acid can be used. In addition, those unidentified microorganisms, unisolated microorganisms, a group of symbiotic microorganisms and newly isolated and identified microorganisms can be also used so long as they have such a characteristic or activity as mentioned above. Already identified microorganisms having such a characteristic or activity and applicable to the present invention include bacteria of genus Pseudomonas, Acinetobactor, Xanthobacter and Renobacter, particularly advantageously used are *Pseudomonas putida, Pseudomonas dehalogenns*, and *Xanthobacter autotrophicus*. Renobacter sp. strain AC (FERM BP-5353; hereafter referred to as strain AC) which is isolated from the Kanto loam soil in Japan, is suitably used in view of its decomposing activity to halogenated organic acids.

TCE-decomposing process of the present invention is applicable to any TCE-polluted materials so long as the microorganism can survive. As is easily understood from the following examples, the cleaning process of the present invention is also applicable to various products, for example, textiles, paper goods and leather goods which can stand the treatment of relatively short period using an aqueous medium, since this process uses the microorganism in an aqueous medium. An example for decomposing TCE in soil or ground water and remedying the soil or ground water, to which the present invention is preferably applicable will now be explained. First, TCE is brought into contact with the above-mentioned bacteria capable of decomposing TCE to form dichloroacetic acid, the resulting dichloroacetic acid is brought in touch with the above-mentioned bacteria capable of decomposing dichloroacetic acid.

Contact between TCE-decomposing bacteria and TCE can be conducted by culturing the microorganism in an aqueous medium containing TCE or adding the aqueous medium and soil to a culture of the microorganism.

Contact between the bacteria capable of decomposing dichloroacetic acid and dichloroacetic acid can be conducted by culturing the microorganism in an aqueous medium in which TCE has already been decomposed by TCE-decomposing bacteria, or adding the aqueous medium and soil to the culture of the microorganism. Various methods such as batch method, semi-continuous method, continuous method and the like can be employed for this process. The microorganism may be used in a half immobilized or fully immobilized state to a suitable carrier.

The process of the present invention is applicable to treating disposal water, soil etc. in both closed system and open system. The microorganism can be used in an immobilized state on a carrier, or other various methods to promoting microbial growth can be concomitantly used.

A number of embodiments of the present invention will now be explained in more detail with reference to the following examples.

In the following examples, halogenated organic acids were determined by high performance liquid chromatography (HPLC) using a column packed with an ion-exchange resin (developed with a solution of 0.01 N sulfuric aqueous solution/acetonitrile=95/5, Detection at 210 nm).

EXAMPLE 1

Decomposition of dichloroacetic acid using Renobacter sp. strain AC

A colony of strain AC grown on the agar medium was inoculated into 100 ml of M9 medium containing 0.1% of yeast extract in a 200 ml Sakaguchi flask (a flat bottom flask with shoulder), and cultured with shaking at 30° C. for 48 hours. The cells of strain AC grew in an aggregated form until about 30 hours, and then started to disintegrate.

Ten samples (Sample Nos. 1–10) were prepared by inoculating 1 ml of the above culture solution into 50 ml of M9 medium containing dichloroacetic acid at 200 ppm, followed by shaking culture at 30° C. From Sample No. 1, one milliliter sample was collected after eight hours of culture and cells was removed by centrifugation, then the supernatant was adjusted to pH 2 or less with dilute sulfuric acid. Then the dichloroacetic acid concentration was measured by HPLC. From Sample No. 2 after 16 hours, from Sample No. 3 after 24 hours and so on, samples were also taken in the same manner to determine the dichloroacetic acid concentration every eight hours, to measure the change of dichloroacetic acid concentration with time.

As shown in FIG. 1, decomposition of dichloroacetic acid started after 8 hours and dichloroacetic acid of 200 ppm was completely decomposed after 48 hours. As an intermediate product, glyoxylic acid was detected, thus confirming the participation of dehalogenase in decomposition. Glyoxylic acid was completely decomposed into carbon dioxide and water in the end.

EXAMPLE 2

Decomposition of other halogenated acetic acids using Renobacter sp. strain AC

Figure 2:
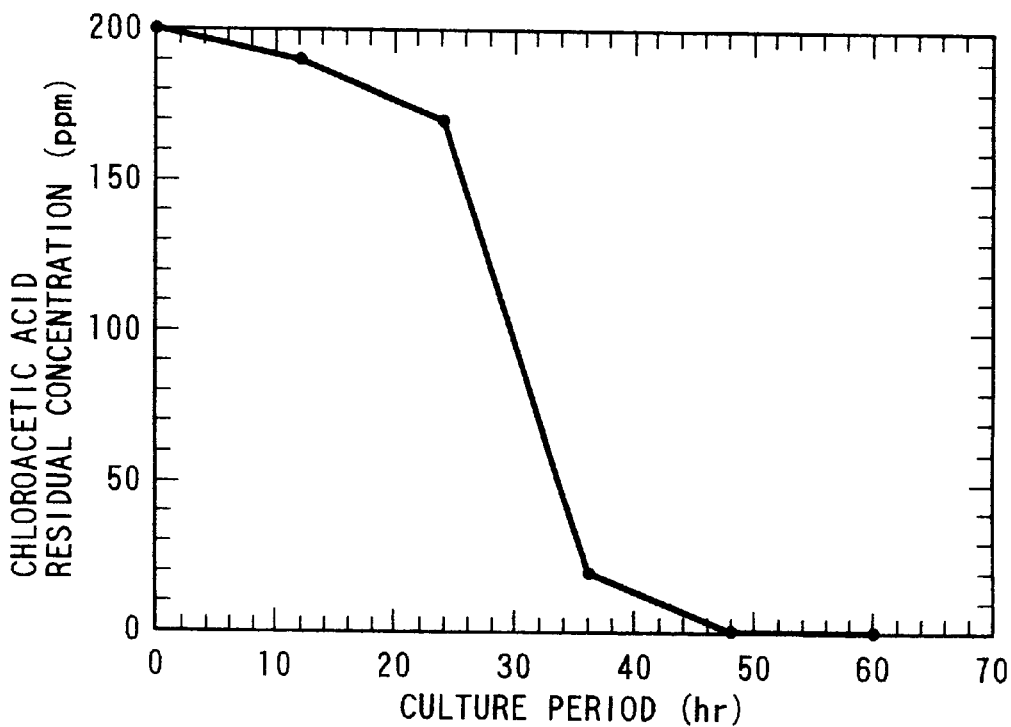
FIG. 2 is a graph showing the decomposition of chloroacetic acid by strain AC.
Figure 3:
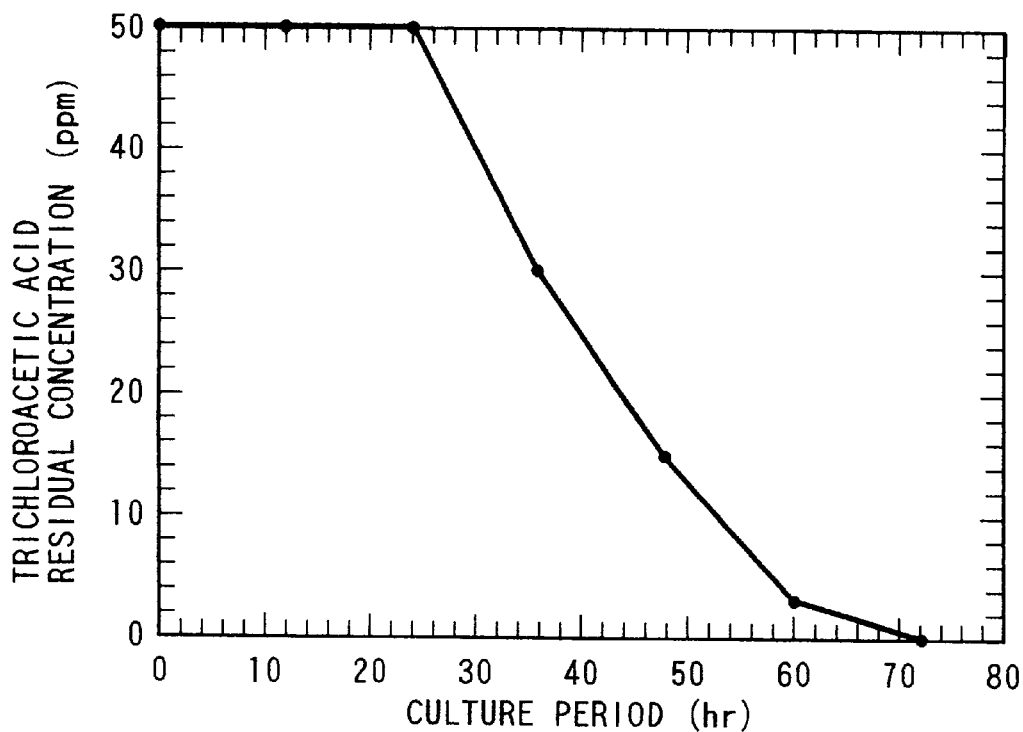
FIG. 3 is a graph showing the decomposition of trichloroacetic acid by strain AC.
Figure 4:
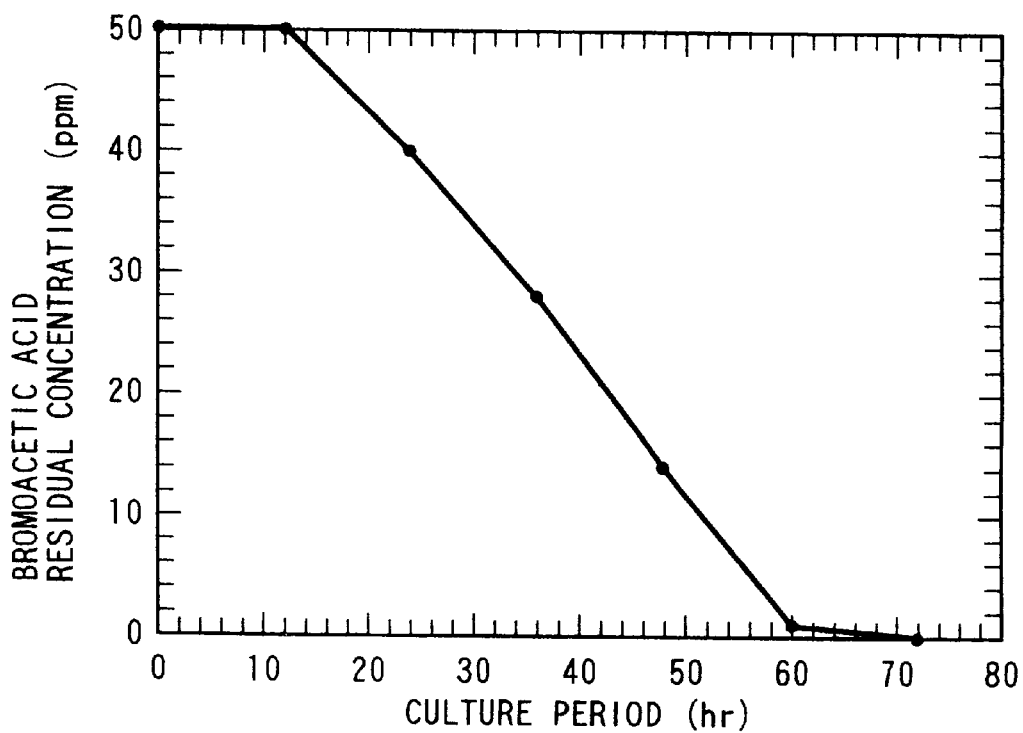
FIG. 4 is a graph showing the decomposition of bromoacetic acid by strain AC.

Chloroacetic acid (200 ppm), trichloroacetic acid (50 ppm) and bromoacetic acid (50 ppm) were subjected to decomposition by strain AC in the same manner as in EXAMPLE 1. The relations between culture period and the concentration of each residual compound are shown in FIGS. 2, 3 and 4 respectively.

These compounds were all completely decomposed within 72 hours. As an intermediate product, glyoxylic acid was detected, thus confirming the participation of dehalogenase in decomposition. Glyoxylic acid was completely decomposed into carbon dioxide and water in the end.

EXAMPLE 3

Figure 5:
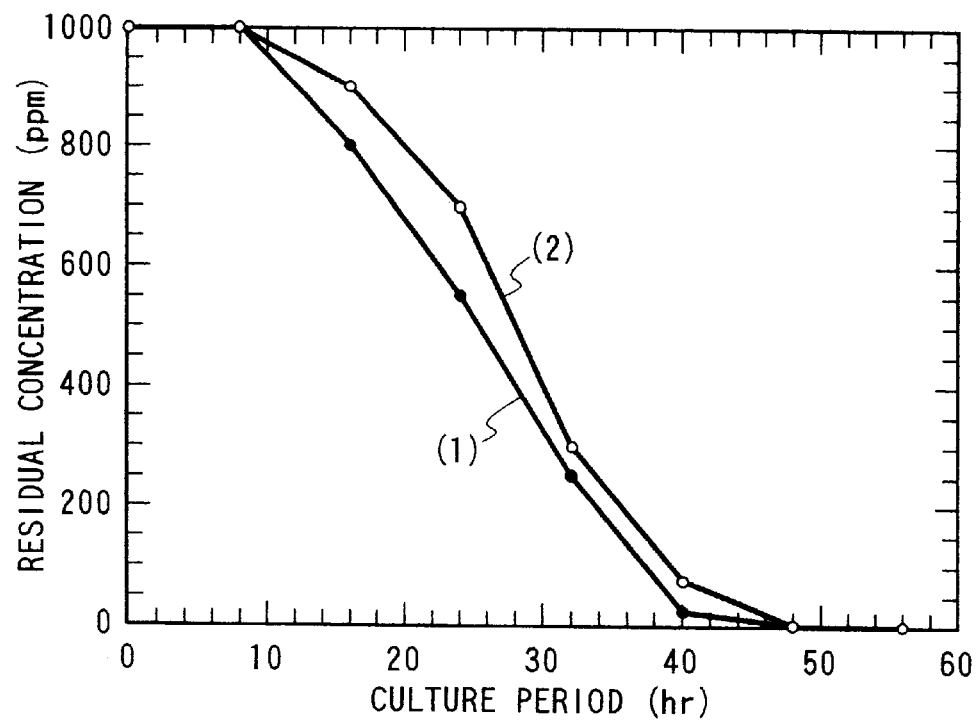
FIG. 5 is a graph showing the decomposition of chloropropionic acid by strain AC.

Decomposition of chloropropionic acid using Renobacter sp. strain AC 2-chloropropionic acid and 3-chloropropionic acid were decomposed by strain AC in the same manner as in EXAMPLE 1. Concentration of each compound was 1000 ppm. The relations between culture period and the residual concentration of each compound are shown in FIG. 5. In FIG. 5, (1) indicates the residual of 2-chloropropionic acid, and (2) the residual concentration of 3-chloropropionic acid.

All these compounds were completely decomposed within 48 hours. As an intermediate product, lactic acid was detected, thus confirming the participation of dehalogenase in decomposition. Lactic acid was completely decomposed into carbon dioxide and water in the end. The lactic acid was completely decomposed into carbon dioxide and water.

EXAMPLE 4

Figure 6:
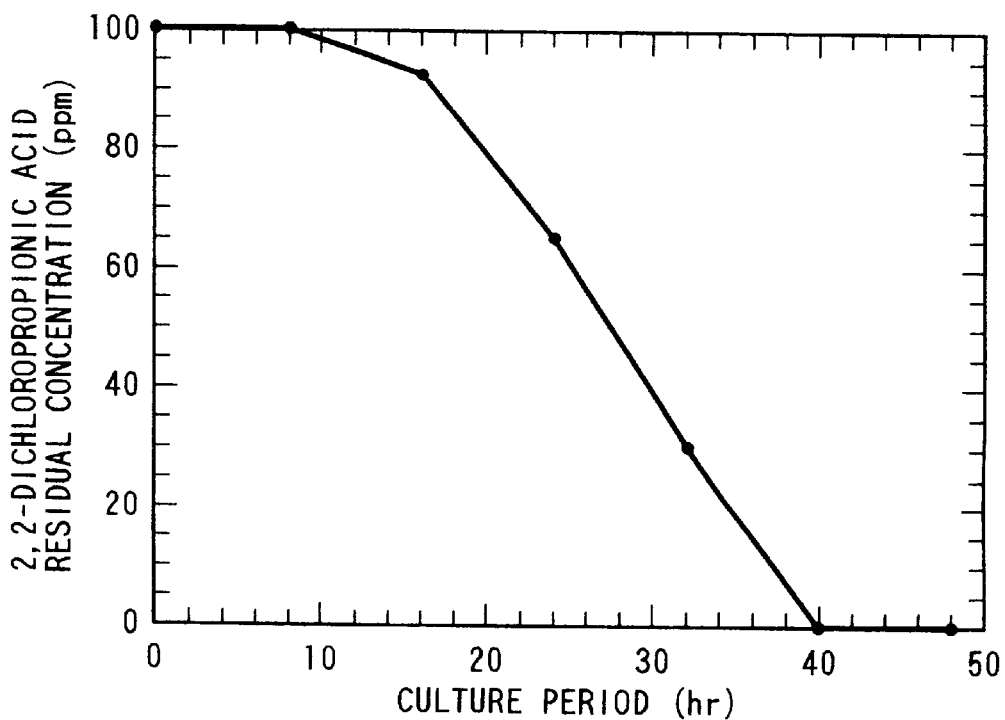
FIG. 6 is a graph showing the decomposition of 2,2-dichloropropionic acid by strain AC.

Decomposition of 2,2-dichloropropionic acid using Renobacter sp. strain AC 2,2-dichloropropionic acid was decomposed using strain AC in the same manner as in EXAMPLE 1. Concentration of the compound was 100 ppm. The relations between culture period and the residual concentration of the compound are shown in FIG. 6.

2,2-dichloropropionic acid (100 ppm) was completely decomposed within 48 hours. As an intermediate product, pyruvic acid was detected, thus confirming the participation of dehalogenase in decomposition. Pyruvic acid was completely decomposed into carbon dioxide and water in the end.

EXAMPLE 5

Remediation of soil polluted with dichloroacetic acid using Renobacter sp. strain AC A colony of strain AC grown on an agar medium was inoculated into 100 ml of M9 medium containing 0.1% yeast extract in a 200 ml Sakaguchi flask, and cultured with shaking at 30° C. for 48 hours. The cells of strain AC grew in an aggregated form for about 30 hours, and then started to disintegrate.

Figure 7:
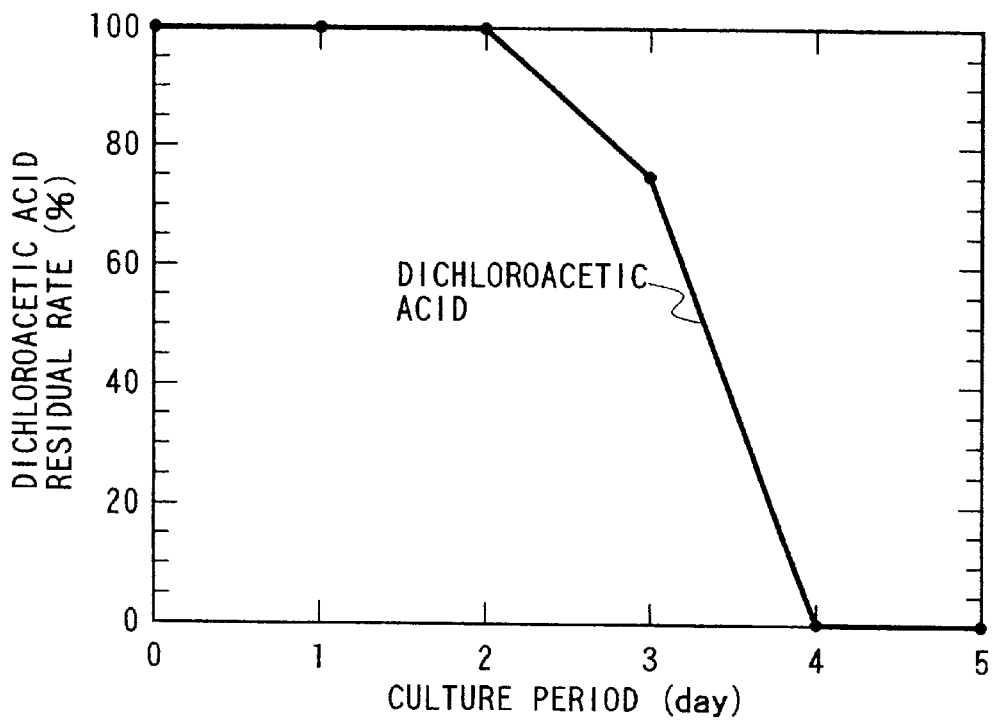
FIG. 7 is a graph showing the decomposition of dichloroacetic acid in soil by strain AC.

Ten milliliter of an aqueous solution of dichloroacetic acid was added to 50 g of air-dried brown forest soil collected in Atsugi-shi, Kanagawaken, Japan to make the dichloroacetic acid concentration 50 mg/g wet soil, to which 10 ml of the above culture solution was mixed and thoroughly stirred, and incubated in a 100 ml conical flask at 30° C. One gram of the soil was taken every 24 hours, to which 5 ml of 0.01 N sulfuric acid aqueous solution was added and stirred for 1 hour. Then the soil was removed by centrifugation and the supernatant was filtered and adjusted to pH 2 or less with dilute sulfuric acid before introducing in HPLC. Thus the daily decrease of dichloroacetic acid was measured. The results are shown in FIG. 7. As a control, an experiment was conducted using a sterile culture medium instead of cell culture, and the residual rate of dichloroacetic acid was expressed by the ratio of the residual dichloroacetic acid to that in the control experiment.

Decomposition began 2 days after and 50 ppm of dichloroacetic acid was completely decomposed after 4 days.

EXAMPLE 6

Figure 8:
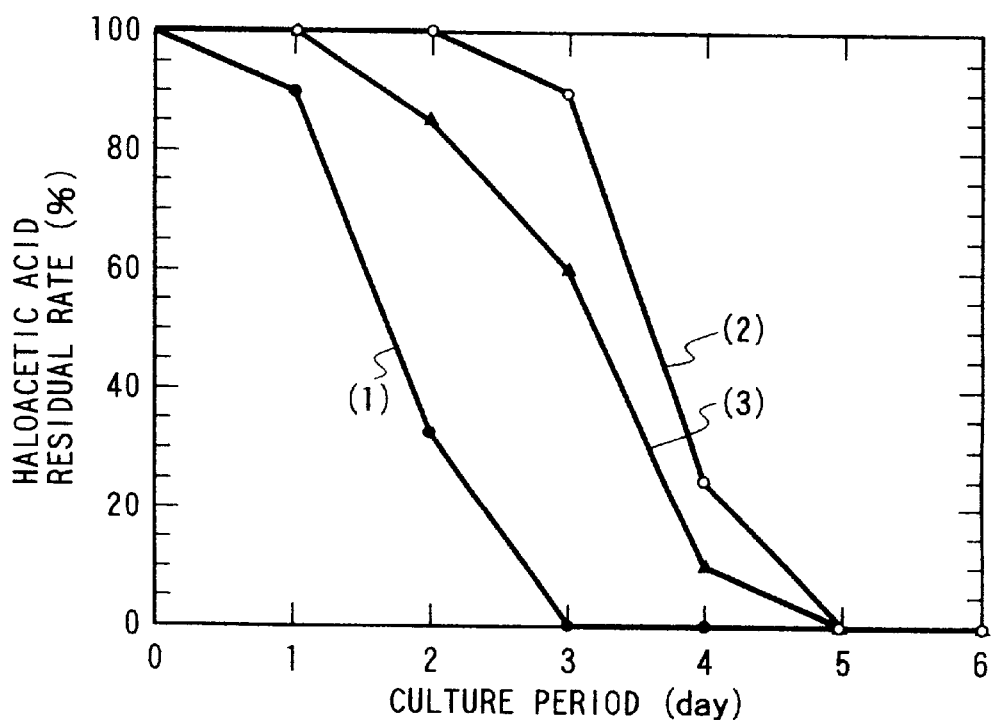
FIG. 8 is a graph showing the decomposition of halogenated acetic acids in soil by strain AC.

Remediation of soil polluted with other halogenated organic acids using Renobacter sp. strain AC An experiment of soil remediation using strain AC was carried out in the same manner as in EXAMPLE 5, where the decomposition subjects were chloroacetic acid (50 ppm), trichloroacetic acid (10 ppm) and bromoacetic acid (10 ppm). The relation between culture period and the residual ratio of these compounds are shown in FIG. 8. In FIG. 8, (1), (2) and (3) indicate residual ratios of chloroacetic acid, trichloroacetic acid and bromoacetic acid, respectively.

Chloroacetic acid was completely decomposed by the third day and trichloroacetic acid and bromoacetic acid by the fifth day of the experiment.

EXAMPLE 7

Figure 9:
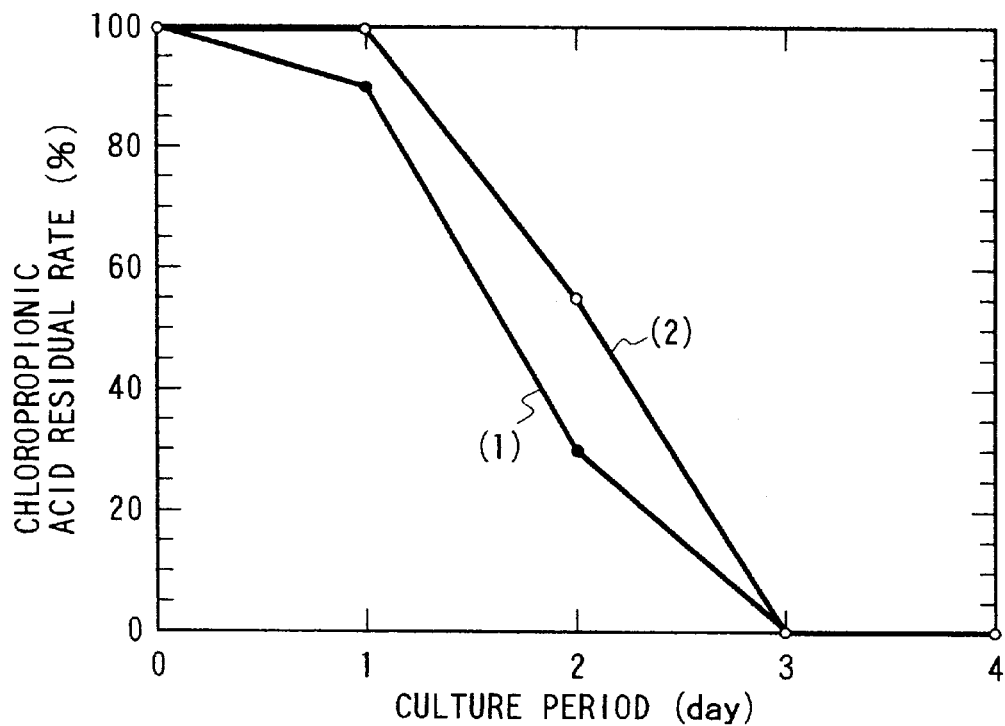
FIG. 9 is a graph showing the decomposition of chloropropionic acids in soil by strain AC.

Decomposition of chloropropionic acid in soil using Renobacter sp. strain AC 2-chloropropionic acid and 3-chloropropionic acid were decomposed using strain AC in the same manner as in EXAMPLE 5. Concentration of each compound was 200 ppm. The relation between culture period and the residual rate of each compound is shown in FIG. 9. In FIG. 9, (1) represents the residual rate of 2-chloropropionic acid and (2) the residual rate of 3-chloropropionic acid.

All these compounds were completely decomposed by the third day.

EXAMPLE 8

Figure 10:
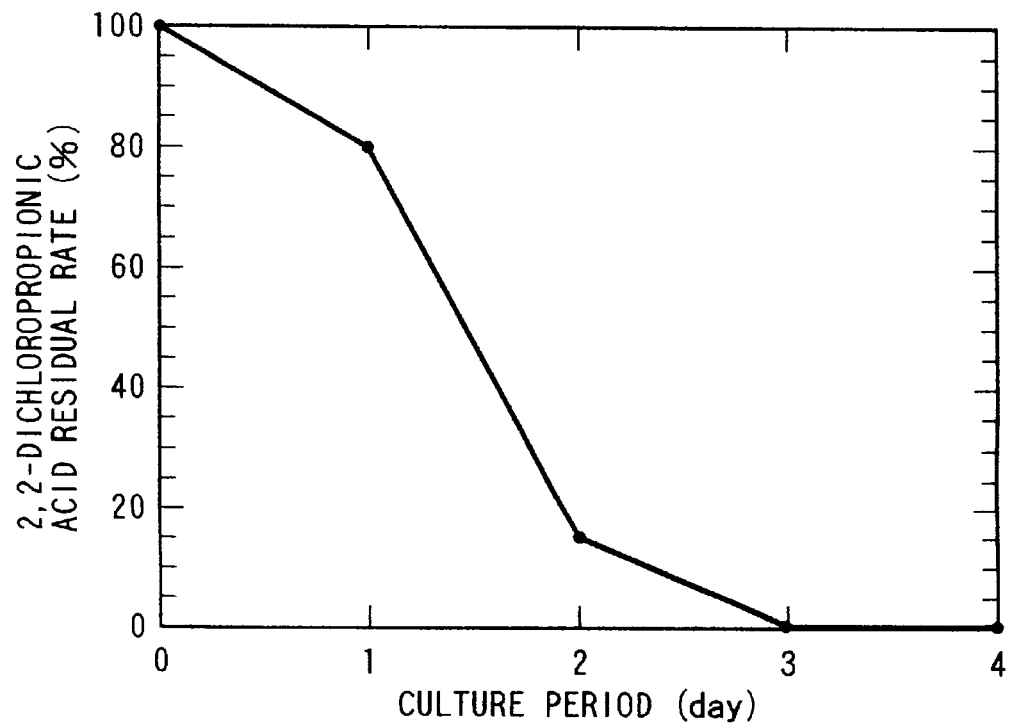
FIG. 10 is a graph showing the decomposition of 2,2-dichloropropionic acid in soil by strain AC.

Decomposition of 2,2-dichloropropionic acid in soil using Renobacter sp. strain AC 2,2-dichloropropionic acid was decomposed using strain AC in the same manner as in EXAMPLE 5. The concentration of the compound was 50 ppm. The relation between culture period and of residual rate of the compound is shown in FIG. 10.

The compound was completely decomposed by the third day.

EXAMPLE 9

Decomposition mechanism of each halogenated organic acid using Renobacter sp. strain AC One milliliter of the same culture broth as used in EXAMPLE 1 was inoculated into each 50 ml of the same culture medium containing dichloroacetic acid, chloroacetic acid, trichloroacetic acid, bromoacetic acid, 2-chloropropionic acid, 3-chloropropionic acid or 2,2-dichloropropionic acid at the same concentration as in Examples 1–4, respectively, and cultured with shaking at 30° C. At an appropriate time, when half of the compound was decomposed, 1 ml of each reaction fluid was collected, the cells were removed by centrifugation and pH was adjusted to pH 2 or less with dilute sulfuric acid. Then the sample was introduced into HPLC to analyze the decomposition intermediates. As a result, formation of following intermediate products were confirmed; glyoxylic acid from dichloroacetic acid, glycolic acid from chloroacetic acid, trichloroacetic acid, and bromoacetic acid, lactic acid from 2-chloropropionic acid, and pyruvic acid from 2,2-dichloropropionic acid (no intermediate product from 3-chloropropionic acid), clearly showing that decomposition of each halogenated organic acid by Renobacter sp. AC strain was due to the action of dehalogenase, a hydrolytic dehalogenating enzyme. It was confirmed that all the above intermediate products were completely decomposed afterwards.

EXAMPLES 10–13 AND COMPARATIVE EXAMPLES 1–3

M9 medium used in Examples 10–13 and Comparative Examples 1–3 has the following composition.

M9 culture medium composition (per one liter)

| | |
|---|---|
| $Na_2HPO_4$ | 6.2 g |
| $KH_2PO_4$ | 3.0 g |
| NaCl | 0.5 g |
| $NH_4Cl$ | 1.0 g |
| water | to 1 liter |
| (pH 7.0) | |

Measurement of TCE concentration was all done by head space gas chromatography. Specifically, 5 ml of M9 medium containing a certain concentration of TCE and 100 μl of cell suspension were put in a 20 ml serum bottle and then the bottle was sealed by a rubber stopper and an aluminum cap, and incubated with shaking at 30° C. for a certain period of time, then 0.1 ml of the gas phase was sampled and measured by gas chromatography. In the examples using soil also, the measurement of TCE concentration was done according to the above method. Dichloroacetic acid was determined as follows: the reaction mixture was adjusted to pH 2 or lower with dilute sulfuric acid and centrifuged. The supernatant was extracted with diethylether and ethyl acetate, and the extract was dried to solid using a rotary evaporator and redissolved in demineralized water. The solution was introduced into a high performance liquid chromatograph (HPLC) with an eluent of 0.01 N aqueous sulfuric acid/acetonitrile=95/5 (v/v). It was confirmed by GC/MS that the peak of eluate observed at the retention time corresponding to the standard dichloroacetic acid in HPLC, corresponds to dichloroacetic acid. In the examples using soil, measurement of dichloroacetic acid was also carried out in the same manner as above except that the soil was directly extracted with diethylether and ethyl acetate.

In the following Examples 10–13 and Comparative Examples 1–3, *Pseudomonas cepacia* strain KK01 (FERM BP-4235) and Corynebacterium sp. strain J1 (FERM BP-5102) were used in addition to Renobacter sp. strain AC (FERM BP-5353) mentioned above.

The above three microbial species have been deposited in the following International Deposition Authority.

Name: National Institute of Bioscience and Human-Technology, Agency of Industrial Science and Technology Address: 1—1, Higashi, 1-chome, Tsukuba-shi, Ibaraki-ken, Japan *Pseudomonas cepacia* strain KK01 was initially deposited as FERM P-12869 on Mar. 11, 1992 and was transferred to Accession No. FERM BP-4235 on Mar. 9, 1993. A complete taxonomic description is found in pending application Ser. No. 08/810,366, filed Mar. 3, 1997. The complete taxonomic description of FERM BP-4235 is as follows:

A. Morphological Properties (1) Gram stain: Negative (2) Size and shape of the bacteria: Bacillus having a length of 1.0–2.0 μm and a width of about 0.5 μm.

(3) Mobility: Present

B. Growth state of the bacteria in each culture medium.

| Culture Medium | Culture Temp. (° C.) | Growth State |
|---|---|---|
| Blood agar culture medium | 37 | + |
| Lactose agar culture medium | 37 | + |
| Chocolate agar culture medium | 37 | ++ |
| GMA | 37 | − |
| Scyllo | 37 | − |
| Usual agar culture medium | 4 | − |
| Usual agar culture medium | 25 | ± |
| Usual agar culture medium | 37 | − |
| Usual agar culture medium | 41 | ± |

C. Physiological properties (1) Aerobic or anaerobic: Strictly aerobic (2) Degradation type of saccharose: Oxidation type (3) Production of oxidase: +

(4) Reduction of silver nitrate: +

(5) Production of hydrogen sulfide: −

(6) Production of indole: −

(7) Production of urease: −

(8) Liquefaction of gelatin: −

(9) Hydrolysis of arginine: −

(10) Decarboxylation of lysine: +

(11) Decarboxylation of ornithine: +

(12) Utilization of citric acid: +

(13) Methylcarbinolacetyl reaction (VP reaction): −

(14) Detection of tryptophane deaminase: −

(15) ONPG: −

(16) Utilization of carbohydrates:
  Glucose: +
  Fruit Sugar: +
  Maltose: +
  Galactose: +
  Xylose: +
  Mannitol: +
  White Sugar: −
  Lactose: +
  Aesculin: −
  Inositol: −
  Sorbitol: −
  Rhamnose: −
  Melibiose: −
  Amygdalin: +
  L-(+)-arabinose: +

Corynebacterium sp. J1 was originally deposited as FERM P-14332 on May 25, 1994 and later transferred to Accession No. FERM BP-5102 on May 17, 1995. A complete taxonomic description is found in allowed application Ser. No. 08/454,515, filed May 30, 1995, now U.S. Pat. No.

5,807,736, issued Sep. 15, 1998. Renobacter sp. strain AC was originally deposited under Accession No. FERM P-14641 on Nov. 15, 1994 and was transferred to Accession No. FERM BP-5353 on Dec. 25, 1995.

The complete taxonomic description of FERM BP-5102 is as follows:

Gram straining and morphology: Gram-negative rod
Growth condition in each medium
BHIA: good
MacConkey: possible
Color of colony: cream
Optimum growth temperature: 25° C.>30° C.>35° C.
Motility: negative (in semisolid medium)
TSI (slant/butt): alkali/alkali, $H_2S(-)$
Oxidase: positive (weak)
Catalase: positive
Fermentation of sugars
   glucose: negative
   sucrose: negative
   raffinose: negative
   galactose: negative
   maltose: negative
Urease: positive
Esculin hydrolysis (β-glucosidase): positive
Nitrate reduction: negative
Indole productivity: negative
Glucose acidification: negative
Arginine dihydrase: negative
Gelatin hydrolysis (protease): negative
β-galactosidase: negative
Assimilation of each compound
glucose: negative
L-arabinose: negative
D-mannose: negative
D-mannitol: negative
N-acetyl-D-glucosamine: negative
maltose: negative
potassium gluconate: negative
n-capric acid: positive
adipic acid: negative
dl-malic acid: positive
sodium citrate: positive
phenyl acetate: negative It is evident that TCE-decomposing strains KK01 and J1 have oxygenase, because they produce 2-hydroxymuconic acid semialdehyde which has maximum absorption at 375 nm as an intermediate product of phenol decomposition. It has been confirmed that this oxygenase participates in decomposition of TCE.

It have been also confirmed from above Examples 1–9 that decomposition of dichloroacetic acid by strain AC was due to the action of dehalogenase, a hydrolytic dehalogenating enzyme.

EXAMPLE 10

Decomposition of TCE and dichloroacetic acid using mixed culture system of strains KK01 and strain AC A colony of strain AC grown on an agar medium was inoculated into 100 ml of M9 medium containing 0.1% of yeast extract in a 200 ml Sakaguchi flask, and cultured with shaking at 30° C. for 48 hours. Then a colony of strain KK01 on an agar medium was inoculated into 100 ml of M9 medium containing 0.1% of yeast extract and 200 ppm of phenol in another 200 ml Sakaguchi flask, and cultured with shaking at 30° C. for 18 hours.

Then the both cells were collected and 100 μl was added to 5 ml of M9 medium containing 10 ppm of TCE in a vial to the each cell density of $6–8\times10^8$ cells/ml. The vial was sealed with a rubber stopper and an aluminum cap and cultured with shaking at 30° C. Measurements of TCE concentration were made every 6 hours in the same manner as mentioned above. At the same time, a suspension of the above two strains was added to 1 liter of M9 medium containing 10 ppm TCE in a Sakaguchi flask to a cell concentration of $6–8\times10^8$ cells/ml and cultured with shaking at 30° C. The dichloroacetic acid concentration was determined every 6 hours in the same manner as mentioned above.

Figure 11:
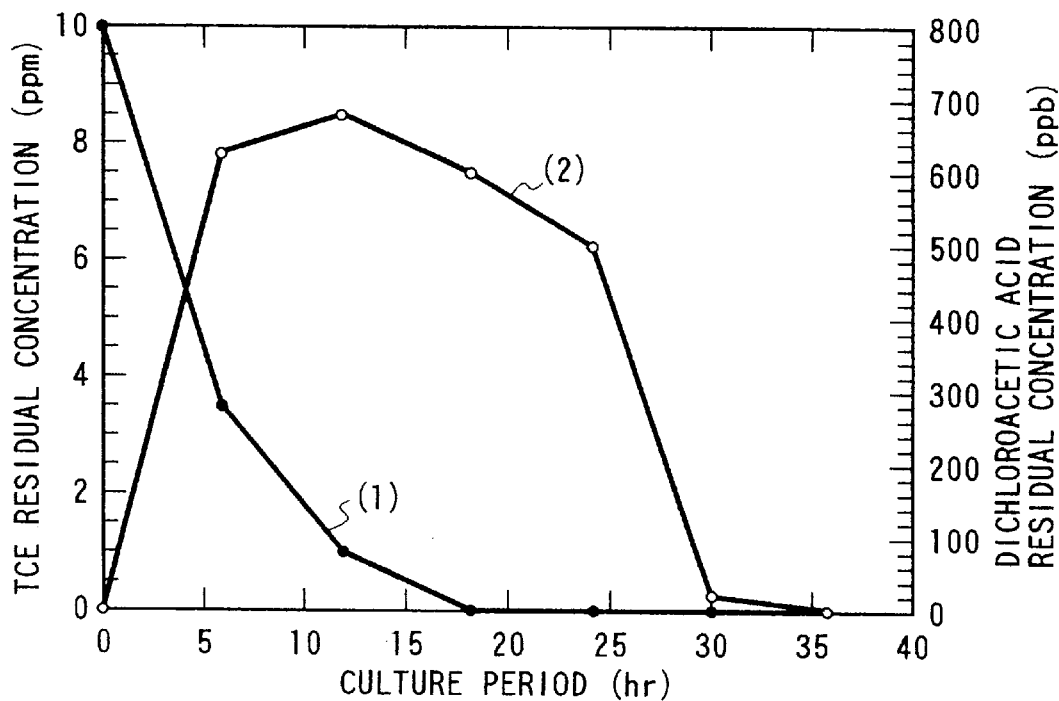
FIG. 11 is a graph showing the results of Example 10.

The results are shown in FIG. 11. Dichloroacetic acid concentration is expressed as a concentration in the original culture. In FIG. 11, (1) indicates the residual concentration of TCE and (2) indicates the residual concentration of dichloroacetic acid.

It was shown that dichloroacetic acid was formed accompanying the decomposition of TCE which was completely decomposed within 16 hours, and decomposed completely within 36 hours.

COMPARATIVE EXAMPLE 1

Decomposition of TCE using strain KK01 and formation of dichloroacetic acid

Concentration of TCE and dichloroacetic acid were measured in the same manner as in EXAMPLE 10 except that only strain KK01 was used.

Figure 12:
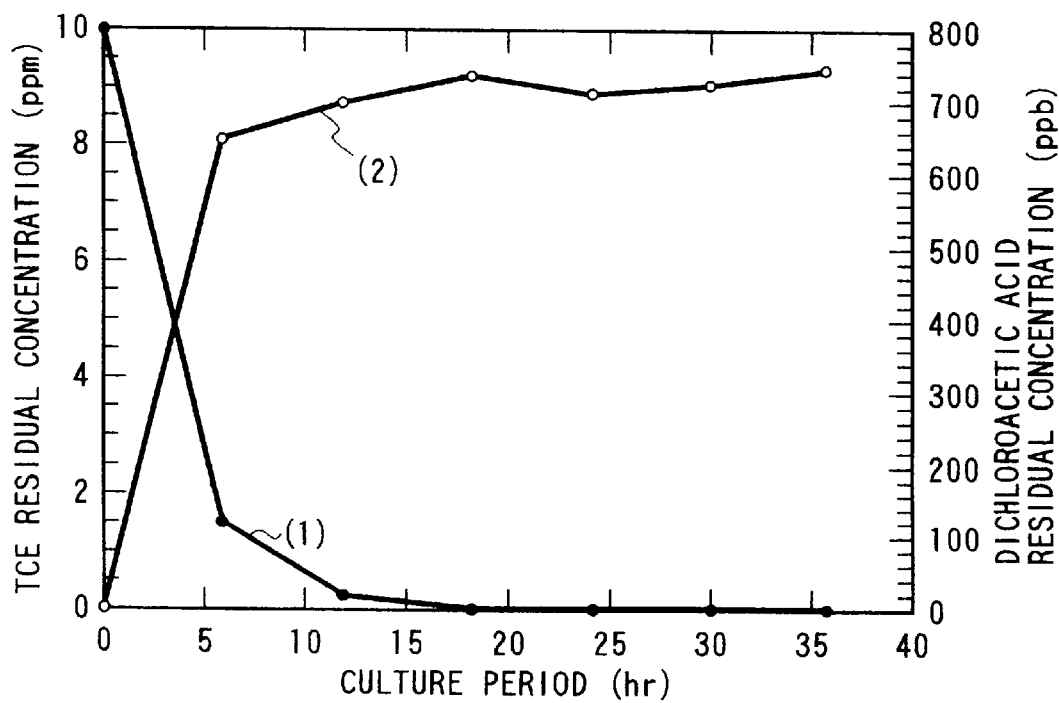
FIG. 12 is a graph showing the results of Comparative Example 1.

The results are shown in FIG. 12. In FIG. 12, the numeral (1) indicates residual concentration of TCE and the numeral (2) indicates that of dichloroacetic acid.

It was revealed that decomposition rate of TCE was a little higher than in a mixed system of strain AC and strain KK01, but that about 700 ppb of dichloroacetic acid remained undecomposed.

EXAMPLE 11

Figure 13:
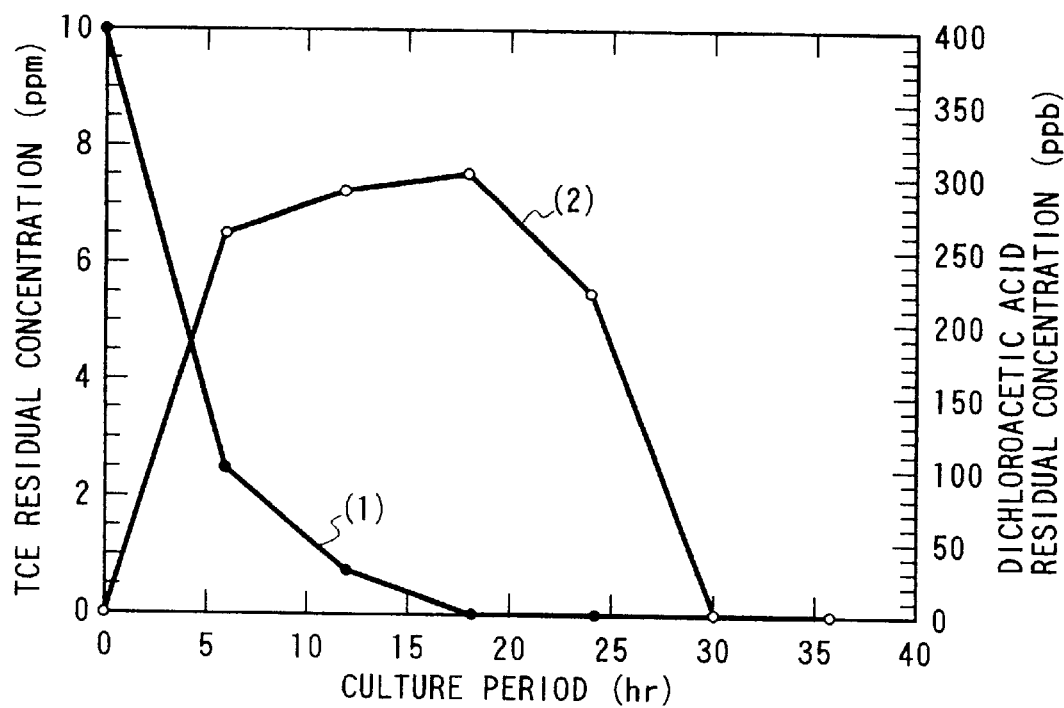
FIG. 13 is a graph showing the results of Example 11.

Decomposition of TCE and dichloroacetic acid in mixed culture system of strain J1 and strain AC Strain J1 and strain AC were inoculated in the same manner as in EXAMPLE 10 and the concentrations of TCE and dichloroacetic acid were measured. The results are shown in FIG. 13. In FIG. 13, the numeral (1) indicates residual concentration of TCE and the numeral (2) indicates that of dichloroacetic acid.

Dichloroacetic acid was formed accompanying the decomposition of TCE which was completely decomposed in 16 hours, and completely decomposed within 30 hours.

COMPARATIVE EXAMPLE 2

Decomposition of TCE using strain J1 and formation of dichloroacetic acid

The concentrations of TCE and dichloroacetic acid were measured in the same manner as in Example 10 except that only strain J1 was used.

Figure 14:
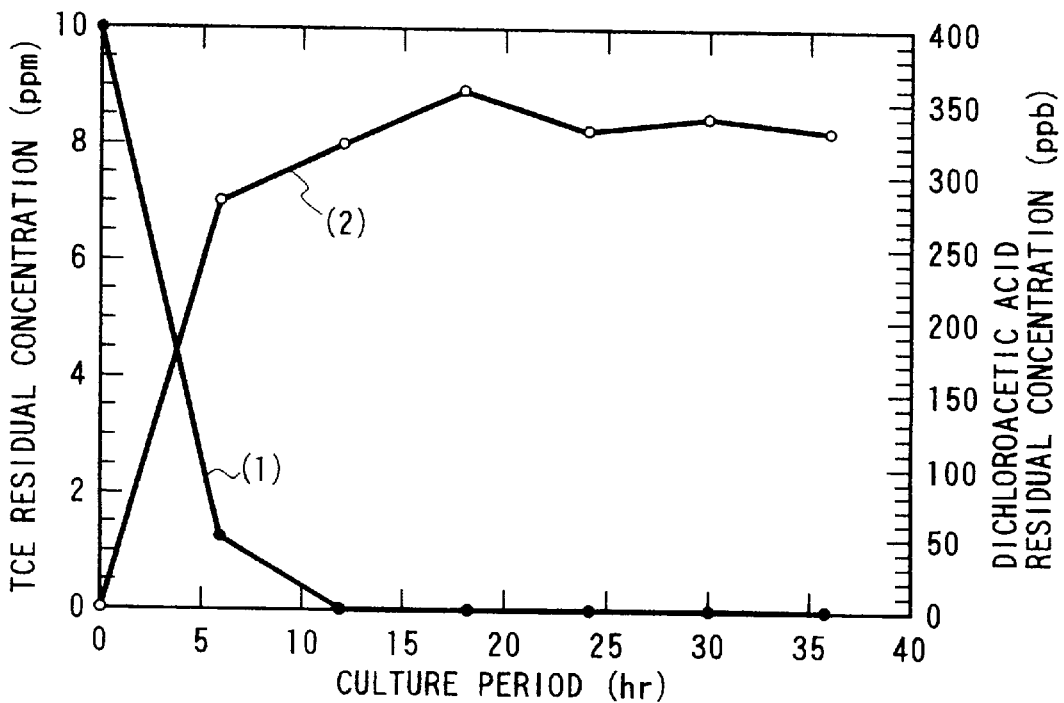
FIG. 14 is a graph showing the results of Comparative Example 2.

The results are shown in FIG. 14. In FIG. 14, the numeral (1) indicates residual concentration of TCE and the numeral (2) indicates that of dichloroacetic acid.

It was revealed that decomposition rate of TCE was a little higher than in a mixed system of strain AC and strain J1, but that about 350 ppb of dichloroacetic acid remained undecomposed.

EXAMPLE 12

Figure 15:
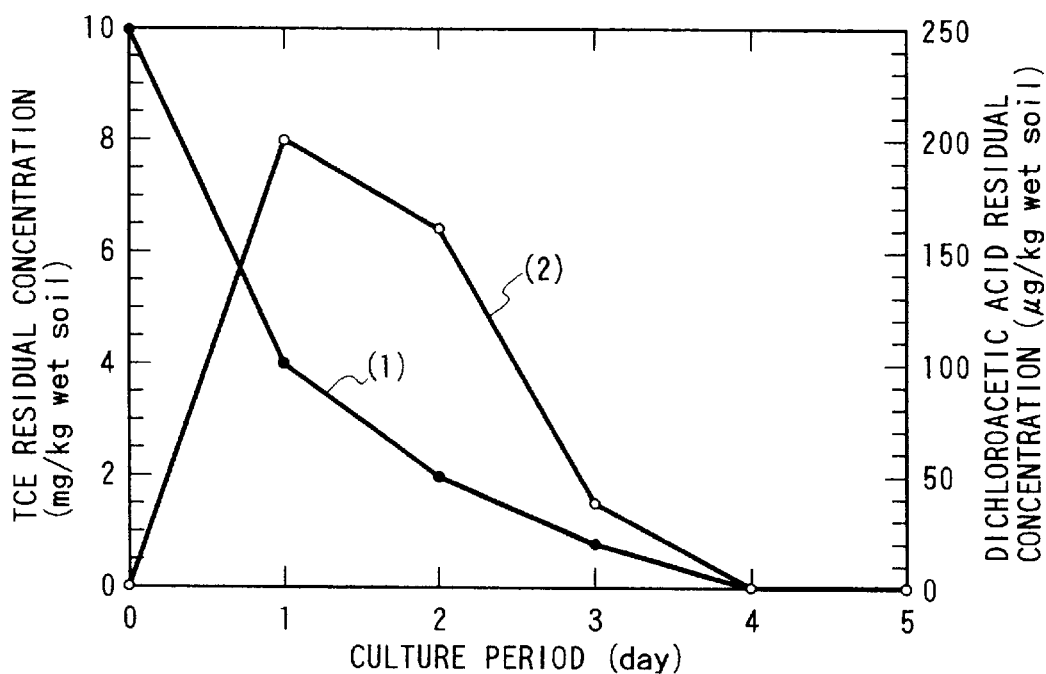
FIG. 15 is a graph showing the results of Example 12.

Decomposition of TCE and dichloroacetic acid in soil in mixed culture system of strain J1 and strain AC Five grams of air-dried brown forest soil collected in Atsugi-shi, Kanagawa-ken, Japan was put in a 20 ml serum bottle and 1 ml of a TCE aqueous solution was added to make the TCE concentration 10 mg TCE/g wet soil. Then the cell suspensions of strain J1 and strain AC prepared in EXAMPLE 11 were inoculated into the soil to each cell concentration of 6–8×10$^8$ cells/g wet soil, and the bottle was sealed with an aluminum cap and incubated at 30° C. The daily change of TCE concentration was determined in the same manner as above. At the same time, 10 ml of an aqueous TCE solution was added to 50 g of air-dried brown forest soil collected in Atsugi-shi, Kanagawa-ken, Japan in make the TCE concentration 10 mg TCE/g wet soil. Then the cells of strain J1 and strain AC prepared in EXAMPLE 11 were inoculated into the soil to each cell concentration of 6–8×10$^8$ cells/g wet soil, and the soil was incubated at 30° C. in an 100 ml serum bottle having a screw cap lined with Teflon liner. One gram of the soil was taken every 24 hours and stirred for one hour in 5 ml of 0.01 N aqueous sulfuric acid, and then the soil was removed by centrifugation and filtration and the resulted liquid was adjusted to pH 2 or below with dilute sulfuric acid and introduced in HPLC. Thus the daily decrease of dichloroacetic acid was measured. The results are shown in FIG. 15. In FIG. 15, the numeral (1) indicates the residual concentration of TCE and the numeral (2) that of dichloroacetic acid.

It was revealed that on the first day the concentration of dichloroacetic acid increased temporarily as TCE was decomposed, but dichloroacetic acid began to undergo decomposition after that and both TCE and dichloroacetic acid were completely decomposed on the fourth day.

COMPARATIVE EXAMPLE 3

Figure 16:
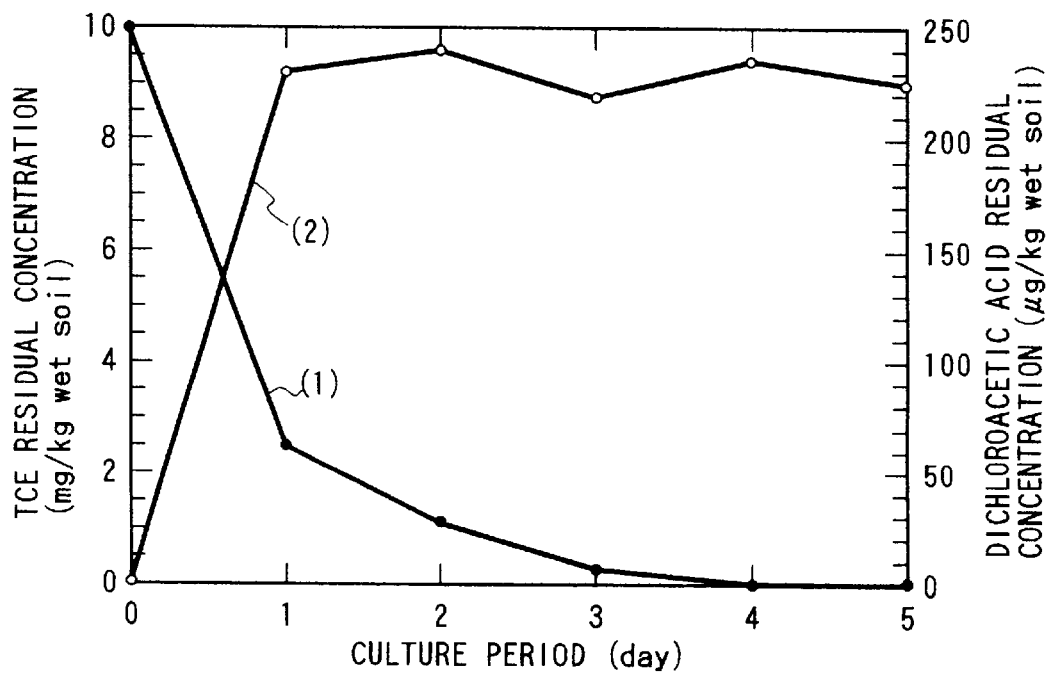
FIG. 16 is a graph showing the results of Comparative Example 3.

Decomposition of TCE in soil using strain J1 and formation of dichloroacetic acid The concentrations of TCE and dichloroacetic acid were measured in the same manner as in Example 12 except that only strain J1 was used. The results are shown in FIG. 16. In FIG. 16, the numeral (1) indicates residual concentration of TCE and the numeral (2) indicates that of dichloroacetic acid.

It was revealed that decomposition rate of TCE was a little higher than in a mixed system of strain AC and strain J1, but dichloroacetic acid remained at about 230 μg/kg wet soil without decomposition.

As described above, the present invention provides a new microbial strain capable of decomposing halogenated organic acids and a process for decomposing halogenated organic acids which is one of the current problems, thus enabling the efficient microbial treatment of the liquid wastes containing halogenated organic acids as well as the soil polluted with halogenated organic acids.

Also according to the present invention, aliphatic organochlorine compounds, particularly trichloroethylene, can be substantially completely decomposed into substances originally present in the natural world, and soil polluted with aliphatic organochlorine compounds can be remedied well.

What is claimed is:

1. A biologically pure culture of Renobacter sp. FERM BP-5353 capable of decomposing halogenated organic acid.

2. A process for remedying environment contaminated with an aliphatic organochlorine compound comprising the steps of:

providing first and second microorganisms which are different from each other, the first microorganism is *Pseudomonas cepacia* strain KK01 (FERM BP-74235) or Corynebacterium sp. (FERM BP-5102) and capable of introducing an oxygen atom into the aliphatic organochlorine compound to convert the aliphatic compound to an epoxide thereof, and the second microorganism is Renobacter sp. (FERM BP-5353) and capable of decomposing a halogenated organic acid to substances naturally existing in nature; and introducing the first and second microorganisms into the environment, wherein the first microorganism converts the aliphatic organochlorine compound into an epoxide thereof, said epoxide being protonized during decomposition thereof to produce a chlorinated organic acid; and wherein the second microorganism converts the chlorinated organic acid into substances naturally existing in nature.

3. The process according to claim 2, wherein the aliphatic organochlorine compound is trichloroethylene.

* * * * *

UNITED STATES PATENT AND TRADEMARK OFFICE
CERTIFICATE OF CORRECTION

PATENT NO. : 6,017,746
DATED : January 25, 2000
INVENTOR(S) : Takeshi Imamura, et al.

It is certified that error appears in the above-identified patent and that said Letters Patent is hereby corrected as shown below:

Title page,
Item [54] in the title, "*SPECIES*" should read -- SPECIES --.
Item [56] OTHER PUBLICATIONS,
"Nakajima et al., "Novel Metabolite of Trichloroethylene..." Pathway", Biosci. Biotech. 56 (3), 486-489. 1992. Meusel et al., "biodegradation of Dichloroacetic acid ...in Soil", Appl. Microbiol. Biotechnol. (1993) 40:165-171." should be deleted.

After "Nelson et al.": "Micron.," should read -- Micro., -- and "aug. 1986," should read -- Aug. 1986 --.

After "Negoro et al.": "Spring 1191," should read -- Spring, 1991, --; after "Hanson et al.": "Sep. 189," should read -- Sep. 1989, --; and after "Motosugi et al.": "(ISSN 0039-9450" should read -- (ISSN 0039-9450) --.

Column 1,
Line 8, "now issued as U.S. Pat. No. 5,679,568" should be deleted.

Column 2,
Line 17, "above" should read -- above- --.

Column 3,
Line 9, "follows:" should read -- follows (identification criteria: according to Burgey's Manual (1984)): --; and
Line 58, "1 litter" should read -- 1 liter --.

Column 5,
Line 43, "fluorescence" should read -- fluorescens --; and
Line 65, "dehalogennas," should read -- dehalogens, --.

Column 6,
Line 37, "to" should read -- of --.

UNITED STATES PATENT AND TRADEMARK OFFICE
CERTIFICATE OF CORRECTION

PATENT NO. : 6,017,746
DATED : January 25, 2000
INVENTOR(S) : Takeshi Imamura, et al.

It is certified that error appears in the above-identified patent and that said Letters Patent is hereby corrected as shown below:

Column 7,
Line 34, "residual" should read -- residual concentration --.

Column 8,
Line 1, "milliliter" should read -- milliliters --;
Line 3, "Kanagawaken," should read -- Kanagawa-ken, --;
Line 55, "of residual" should read -- the residual --.

Column 9,
Line 9, "confirmed;" should read -- confirmed: --.

Column 10,
Line 2, "Japan *Pseudomonas*" should read --Japan. *Pseudomenas*--.

Column 11,
Line 53, "have" should read -- has --.

Column 13,
Line 12, "in" (second occurrence) should read -- to --.

Column 14,
Line 24, " (FERM BP-74235) " should read -- (FERM BP-4235) --.

Signed and Sealed this

Thirtieth Day of October, 2001

Attest:

NICHOLAS P. GODICI
*Attesting Officer*    *Acting Director of the United States Patent and Trademark Office*